(12) United States Patent
Takagi et al.

(10) Patent No.: US 7,177,388 B2
(45) Date of Patent: Feb. 13, 2007

(54) COMPUTED TOMOGRAPHY SYSTEM

(75) Inventors: Hiroyuki Takagi, Takahagi (JP); Katsutoshi Satoh, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/302,169

(22) Filed: Dec. 14, 2005

(65) Prior Publication Data
US 2006/0133565 A1 Jun. 22, 2006

(30) Foreign Application Priority Data
Dec. 17, 2004 (JP) ............................ 2004-365604

(51) Int. Cl.
*G01N 23/00* (2006.01)
(52) U.S. Cl. ............................ 378/20; 378/4
(58) Field of Classification Search .............. 378/4–20, 378/208–209, 177
See application file for complete search history.

(56) References Cited
U.S. PATENT DOCUMENTS
6,327,328 B1 12/2001 Satoh et al.

FOREIGN PATENT DOCUMENTS
| JP | 360256034 A | * 12/1985 |
| JP | 62067432 A | * 3/1987 |
| JP | 6-80420 | 10/1994 |

* cited by examiner

*Primary Examiner*—Edward J. Glick
*Assistant Examiner*—Hoon Song
(74) *Attorney, Agent, or Firm*—Antonelli, Terry, Stout and Kraus, LLP.

(57) ABSTRACT

The present invention provides a computed tomography system that only requires rotational scans for image pickup, the system enabling images of a plurality of testing objects to be simultaneously picked up without increasing the volume of noise or the scale of the system, thus enabling high-quality tomographic images to be efficiently picked up. In the computed tomography system, a plurality of turn tables 11*a* to 11*d* are provided in a region of irradiation with X-ray beams emitted by an X-ray irradiation system. Testing objects Ma to Md are placed on the respective turn tables. Images of the plurality of testing objects can be simultaneously picked up by irradiation with X-ray beams. This enables precise image pickup to be efficiently achieved without increasing the size of the scale.

3 Claims, 5 Drawing Sheets

COMPUTED TOMOGRAPHY SYSTEM

BACKGROUND OF THE INVENTION

The present invention relates to a computed tomography system typified by an X-ray computed tomography system, and in particular, to a computed tomography system effective in increasing the image pickup efficiency of an image pickup system that only requires a testing object to be rotated in order to acquire data required to reconstruct images.

Owing to the history of development, some X-ray computed tomography systems use a 1st or 2nd generation image pickup system and others use a 3rd or 4th generation image pickup system. To acquire all the data required to reconstruct images, the 1st or 2nd generation image pickup system needs to translate and rotate a testing object. In contrast, the 3rd and 4th generation image pickup system has only to rotate the testing object. FIG. 4 schematically shows a conventional general configuration of a third-generation X-ray computed tomography system. The X-ray computed tomography system comprises an X-ray irradiation system 1, a turn table 2, and an X-ray detection system 3. The X-ray irradiation system 1, serving as a radiation irradiation system, irradiates a testing object M placed on the turn table 2 with an X-ray beam (in the illustrated example, a fan beam that fans out) 4 which serve as a radiation and which radiates in the direction of irradiation, the X-ray beam 4 having a predetermined region of irradiation. The spread of the region of irradiation with the X-ray fan beam 4 depends on the size of the X-ray detection system 3. The testing object M is irradiated with the X-ray fan beam 4 while being rotated relative to the X-ray irradiation system 1 and X-ray detection system 3 using the turn table 2. More specifically, the applied X-ray fan beam 4 is in the form of a pulse that synchronizes with a rotational position signal from the turn table 2. The pulse has a width of about 5 microseconds and an interval of, for example, about 5 milliseconds. An X-ray having penetrated the testing object M then enters the X-ray detection system 3. The X-ray detection system 3, serving as a radiation detection system, is composed of a plurality of X-ray detectors 5 linearly arranged at a predetermined pitch. Each of the X-ray detectors 5 detects the intensity of the X-ray. Each X-ray detector 5 outputs a signal corresponding to the detected intensity of the X-ray. Then, an image reconstruction system (not shown) executes an image reconstruction process on X-ray penetration data obtained on the basis of an output signal from each X-ray detector 5 to create a tomographic image of the testing object M.

Such an X-ray computed tomography system is based on an operation of picking up a tomographic image of one testing object placed on the turn table 2. Accordingly, when images of a plurality of testing objected are to be picked up, the corresponding amount of time is required for the image pickup. Thus, the X-ray computed tomography system does not operate efficiently when dealing with a large number of testing objects as in the case of, for example, product inspections on a production line.

Such a system as shown in FIG. 5 is known in connection with the improvement of the efficiency with which images of a plurality of testing objects are picked up. This system is applicable to the case in which the testing object M is sufficiently smaller than the turn table 2. That is, the fact that the testing object M is sufficiently smaller than the turn table 2 is utilized to place a plurality of testing objects M on the turn table 2 so that images of these testing objects M are simultaneously picked up. This makes it possible to reduce the time required to pick up an image of each testing object, thus improving image pickup efficiency.

Further, a system disclosed in JP-B-6-80420 is also known in connection with the improvement of the efficiency with which images of a plurality of testing objects are picked up. According to the system disclosed in JP-B-6-80420, a plurality of turn tables are installed in a direction in which testing objects are translated (linear reciprocation direction) so that images of the testing objects placed on the turn tables can be sequentially picked up. This improves the image pickup efficiency.

The image pickup efficiency improving system shown in FIG. 5 poses the following problem. The position of the testing object varies in the direction of irradiation with an X-ray as the turn table rotates. This results in an unwanted increase in the length of an X-ray path. As a result, the adverse effect of noise becomes more serious to degrade the quality of tomographic images. Further, when the number of testing objects placed on the turn table is increased in order to improve image pickup efficiency, it is unavoidable that during irradiation with an X-ray, one testing object is in the shadow of another, that is, an X-ray having penetrated one testing object penetrates another again. This also increases the length of the X-ray penetration path to make the adverse effect of noise more serious, thus degrading the quality of tomographic images. These problems can be avoided by increasing the intensity of the X-ray. However, this very disadvantageously increases the scale of the system. That is, in the system in which a plurality of testing objects are placed on one table to improve the image pickup efficiency, an attempt to increase image pickup precision disadvantageously results in an increase in the size of the system. In contrast, an attempt to avoid an increase in the scale of the system disadvantageously makes precise image pickup difficult.

On the other hand, the system disclosed in JP-B-6-80420 can avoid these problems. However, the system disclosed in JP-B-6-80420 is based on the 1st or 2nd generation system. Accordingly, the system disclosed in JP-B-6-80420 is effective on the 1st or 2nd generation system but is not expected to improve the image pickup efficiency of the 3rd or subsequent generation system.

SUMMARY OF THE INVENTION

The present invention is made in view of these circumstances. It is thus an object of the present invention to provide a computed tomography system that only requires a testing object to be rotated in order to acquire data required to reconstruct images, the system enabling images of a plurality of testing objects to be simultaneously picked up without increasing the volume of noise or the scale of the system, thus enabling high-quality tomographic images to be efficiently picked up.

To accomplish this object, the present invention provides a computed tomography system comprising a radiation irradiation system that provides a radiation that is a beam having a region of irradiation spreading radially in a direction of irradiation, a turn table system on which a testing object is placed, and a radiation detection system that detects the radiation having penetrated the testing object, the radiation being applied to the testing object being rotated using the turn table system, the radiation detection system detecting the radiation in the irradiation to acquire radiation penetration data for image reconstruction, the computed tomography system being characterized in that a plurality of turn tables are provided in the region of irradiation with the radiation beams.

Further, according to the present invention, in the above computed tomography system, the plurality of turn tables are arranged in a relationship such that during irradiation with the radiation, each of the testing objects placed on the respective turn tables is not in a shadow of another testing object.

To accomplish this object, the present invention provides a computed tomography system comprising a radiation irradiation system that provides a radiation that is a beam having a region of irradiation spreading radially in a direction of irradiation, a turn table system on which a testing object is placed, and a radiation detection system that detects the radiation having penetrated the testing object, the radiation being applied to the testing object being rotated using the turn table system, the radiation detection system detecting the radiation in the irradiation to acquire radiation penetration data for image reconstruction, the computed tomography system being characterized in that the turn table system comprises one large turn table and a plurality of small turn tables, and the large and small turn tables can be selectively used.

Further, according to the present invention, in the computed tomography system as described above, the plurality of small turn tables can be installed on the large turn table, as required, via attachment portions provided on the large turn table.

Furthermore, according to the present invention, in the computed tomography system as described above, the plurality of small turn tables is arranged in the region of irradiation with the radiation beam, and the large turn table can be installed above the plurality of small turn tables, as required, via an attachment portion provided in the region of irradiation with the radiation beams.

In the present invention, the plurality of turn tables are provided in the region of irradiation with radiation beams. Thus, the present invention enables the pickup of images of a plurality of testing objects the number of which corresponds to the number of turn tables. This increases image pickup efficiency. Further, one testing object is placed on each of the plurality of turn tables for image pickup. This serves to fix the position of each testing object in the direction of irradiation with the radiations. It is thus possible to avoid an unwanted increase in the length of the radiation path and to avoid the situation in which one testing object is in the shadow of another. Therefore, the present invention enables precise image pickup to be efficiently achieved without increasing the scale of the system.

Further, in the present invention, the one large turn table and the plurality of small turn tables are provided so as to be selectively used. Thus, according to the present invention, the different turn tables are used depending on the size of the testing objects to allow the images of a plurality of small testing objects to be simultaneously picked up. This enables precise image pickup to be efficiently achieved without increasing the scale of the system. It is also possible to deal with large testing objects to improve generous purpose properties.

Other objects, features and advantages of the invention will become apparent from the following description of the embodiments of the invention taken in conjunction with the accompanying drawings.

DETAILED DESCRIPTION OF THE INVENTION

Figure 1:
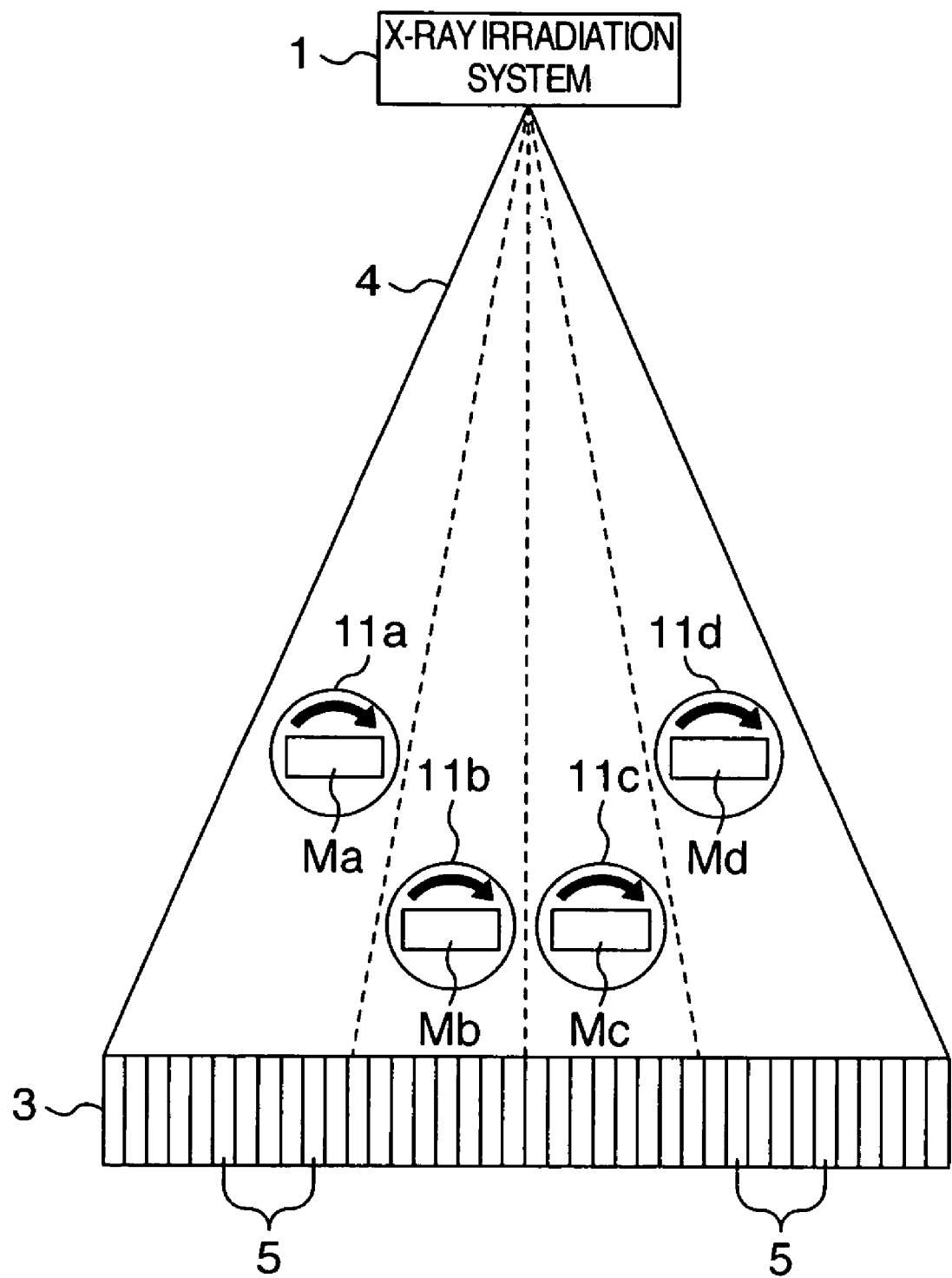
FIG. 1 is a diagram schematically showing the configuration of a computed tomography system in accordance with a first embodiment.
Figure 4:
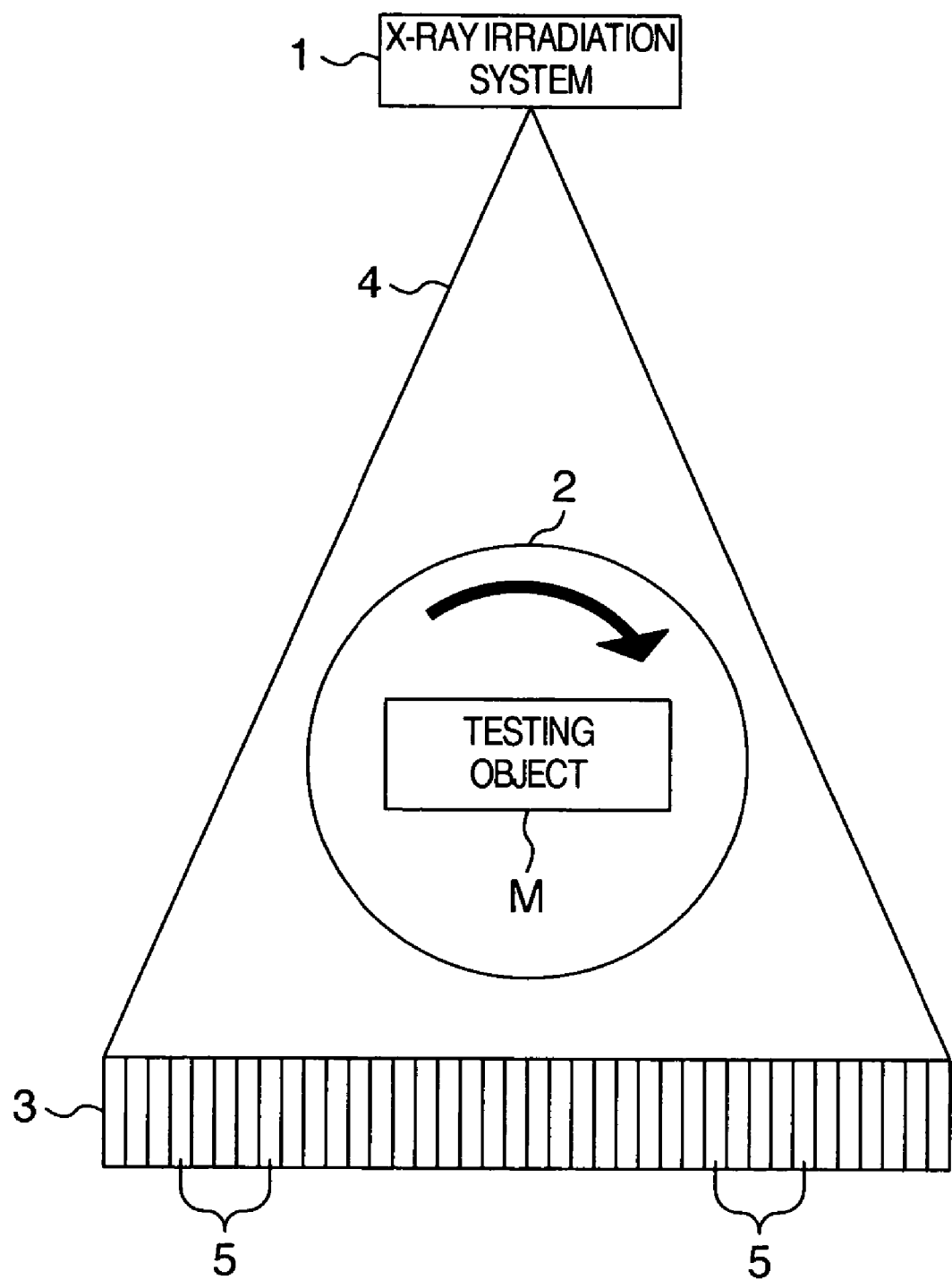
FIG. 4 is a diagram schematically showing a general configuration of a conventional X-ray computed tomography system.
Figure 5:
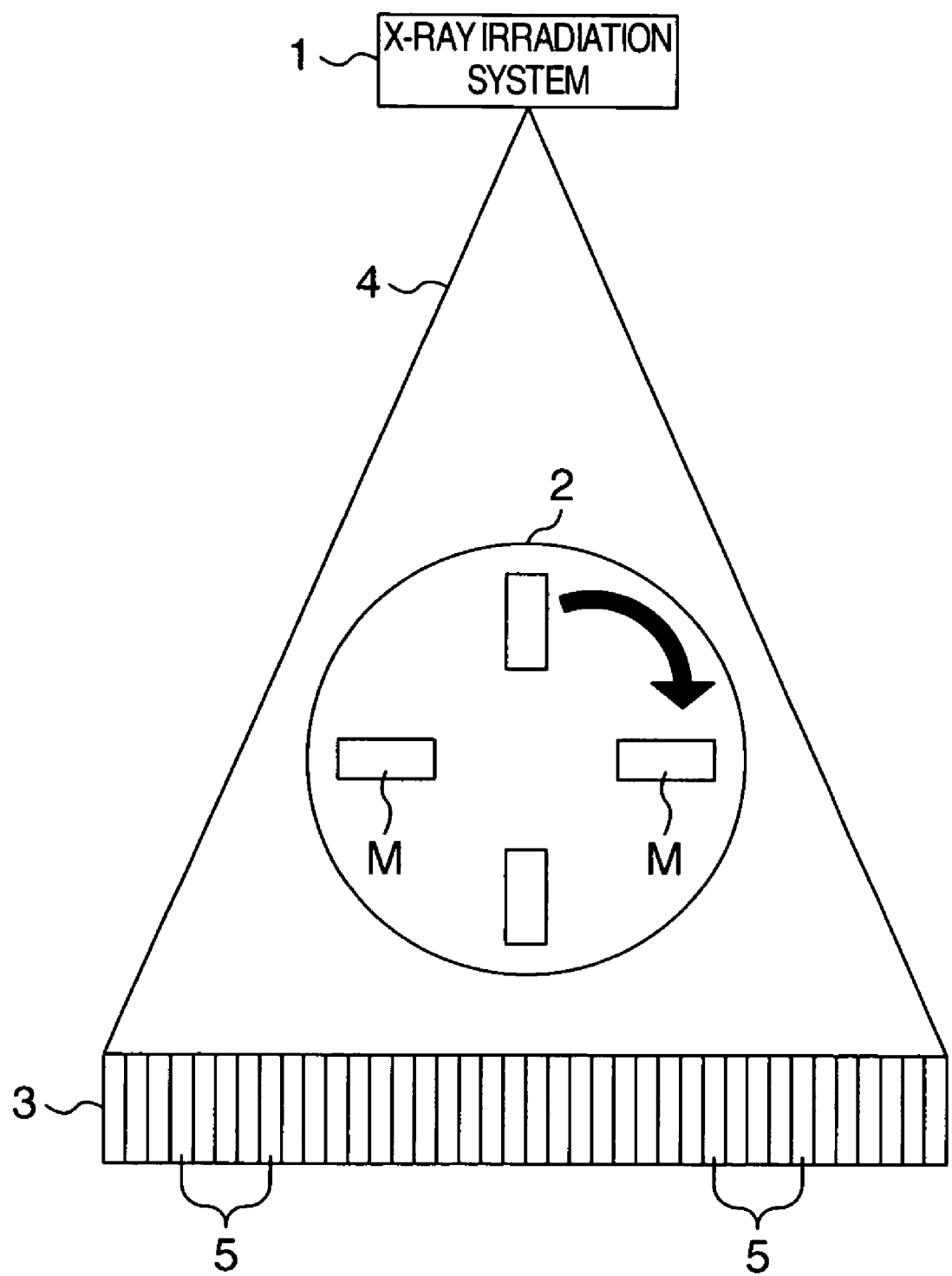
FIG. 5 is a diagram showing a conventional system that simultaneously picks up images of a plurality of testing objects.

Embodiments of the present invention will be described. FIG. 1 schematically shows the configuration of a computed tomography system in accordance with a first embodiment. The computed tomography system in accordance with the present embodiment is an X-ray computed tomography system and has the same arrangements as those of the conventional X-ray computed tomography system described for FIG. 4. Arrangements characteristic of the present embodiment will mainly be described below. For the same arrangements as those of the conventional X-ray computed tomography system, read the above description; the description of these arrangements will be appropriately omitted below. The X-ray computed tomography system in accordance with the present embodiment comprises a plurality of, specifically, four turn tables 11a to 11d. The turn tables 11a to 11d are fixedly arranged within the region of irradiation with fan beams 4. Further, the turn tables 11a to 11d are arranged in a relationship such that during irradiation with X-rays, each testing object M (Ma to Md) placed on one of the turn tables is not in the shadow of another testing object, that is, such that an X-ray having penetrated one testing object does not penetrate another again.

Such an X-ray computed tomography system picks up images as described below. The four turn tables 11 are provided, so that images of up to four testing objects can be simultaneously picked up. The testing objects are, for example, inspecting objects for product inspections on a production line. A tomographic image pickup target region is predetermined for each testing object. The testing objects are placed on the respective turn tables 11a to 11d so that the respective image pickup target regions are at the same height level. Then, the four turn tables 11a to 11d are synchronously rotated, while the fan beams 4 are applied in the form of pulses in synchronism with the angle of the rotation. The pulse has a width of, for example, about 5 microseconds and an interval of, for example, about 5 milliseconds. X-rays having penetrated the four testing objects Ma to Md enter X-ray detectors 5 located at the corresponding positions in an X-ray detection system 3, to detect their intensities. Each of the X-ray detectors 5 outputs a signal corresponding to the detected intensity of the X-ray. Then, an image reconstruction system (not shown) executes an image reconstruction process on X-ray penetration data obtained on the basis of the output signal from each X-ray detector 5. The image reconstruction system thus creates a tomographic image of each of the testing objects Ma to Md.

In such image pickup, if the time required for rotation for one scan is, for example, 10 seconds, 2.5 seconds is required to pick up a tomographic image of one testing object. That is, with the X-ray computed tomography system in accordance with the present invention in which a plurality of turn tables are provided in the region of irradiation with the X-ray fan beams 4, for n turn tables and the time t required for rotation for one scan, it is possible to set the time required to pick up a tomographic image of a testing object at t/n. This makes it possible to improve image pickup efficiency.

In the X-ray computed tomography system in accordance with the present invention, one testing object is placed on each of the plurality of turn tables. This serves to fix the position of each testing object in the direction of irradiation with X-rays. It is thus possible to avoid an unwanted increase in the length of X-ray paths which may occur if a plurality of testing objects are placed on one table. Further, the turn tables can be easily arranged so that the testing object on one turn table is not in the shadow of the testing object on another turn table. This makes it possible to avoid the situation in which during irradiation with X-rays, one testing object is in the shadow of another. Therefore, precise image pickup can be efficiently achieved without increasing the scale of the system.

Figure 2:
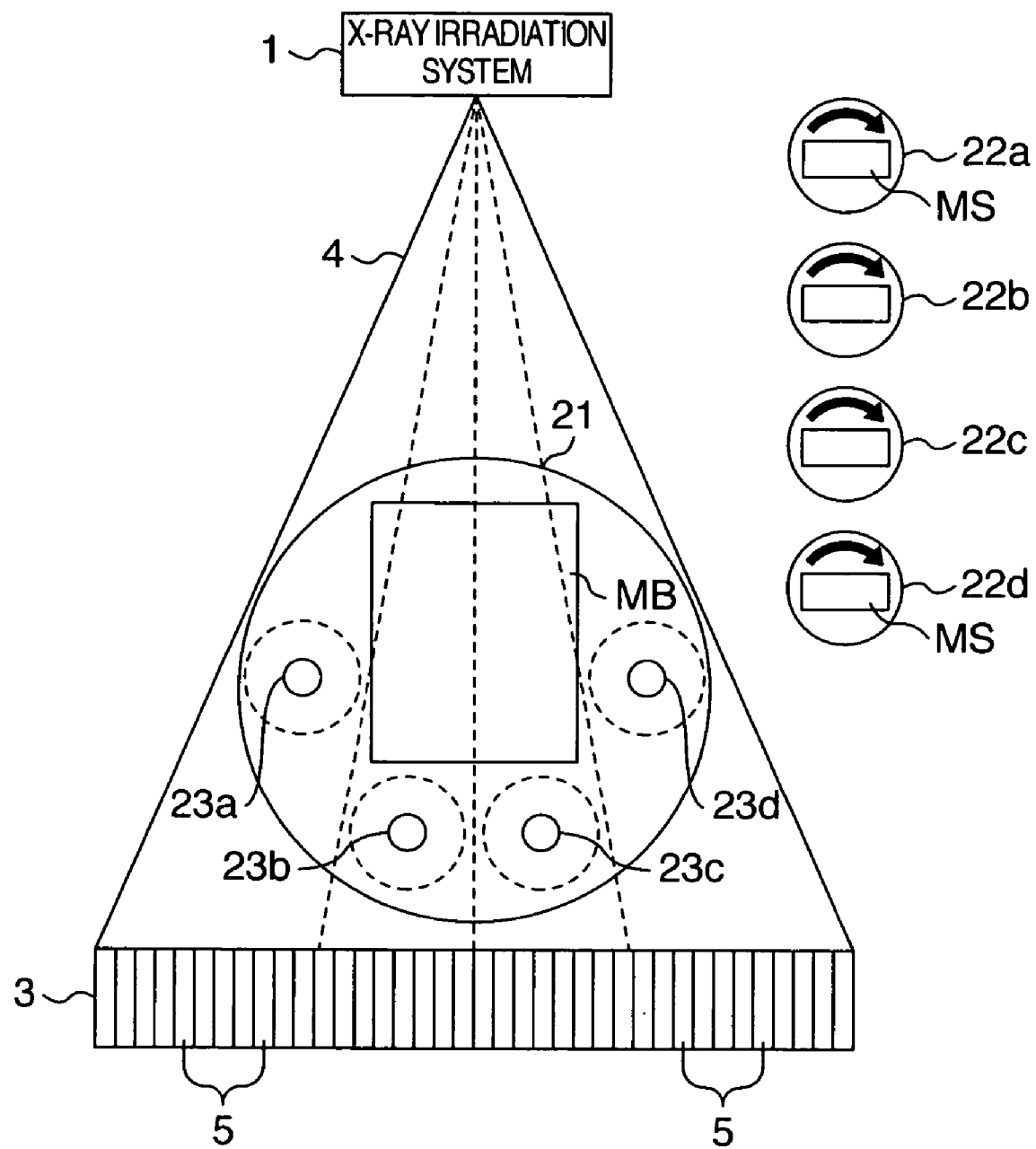
FIG. 2 is a diagram schematically showing the configuration of a computed tomography system in accordance with a second embodiment.

FIG. 2 schematically shows the configuration of an X-ray computed tomography system that is a computed tomography system in accordance with a second embodiment. The X-ray computed tomography system in accordance with the present embodiment comprises one large turn table 21 and a plurality of, specifically, four small turn tables 22*a* to 22*d*. The large turn table 21 and the small turn tables 22 can be selectively used. Specifically, attachment portions 23 (23*a* to 23*d*) are provided on the large turn table 21. The small turn tables 22 can be installed on the large turn table 21 as required via the attachment portions 23 so as to be covered by the region of irradiation with the fan beams 4.

Such an X-ray computed tomography system picks up images as described below. If testing objects that are image pickup targets are large, only one testing object MB is placed on the large turn table 21 for image pickup. On the other hand, if testing objects that are image pickup targets are small, the attachment portions 23 are used to install a required number of small turn tables 22 on the large turn table 21. The small testing objects MS are then placed on the respective small turn tables 22. Then, images are picked up as described in the first embodiment.

Thus, according to the present embodiment, the large turn table 21 and the small turn tables 22 are selectively used to enable image pickup in accordance with the size of the testing object. For small testing objects, the present embodiment can increase the image pickup efficiency for a plurality of image pickup targets similarly to the first embodiment.

Figure 3:
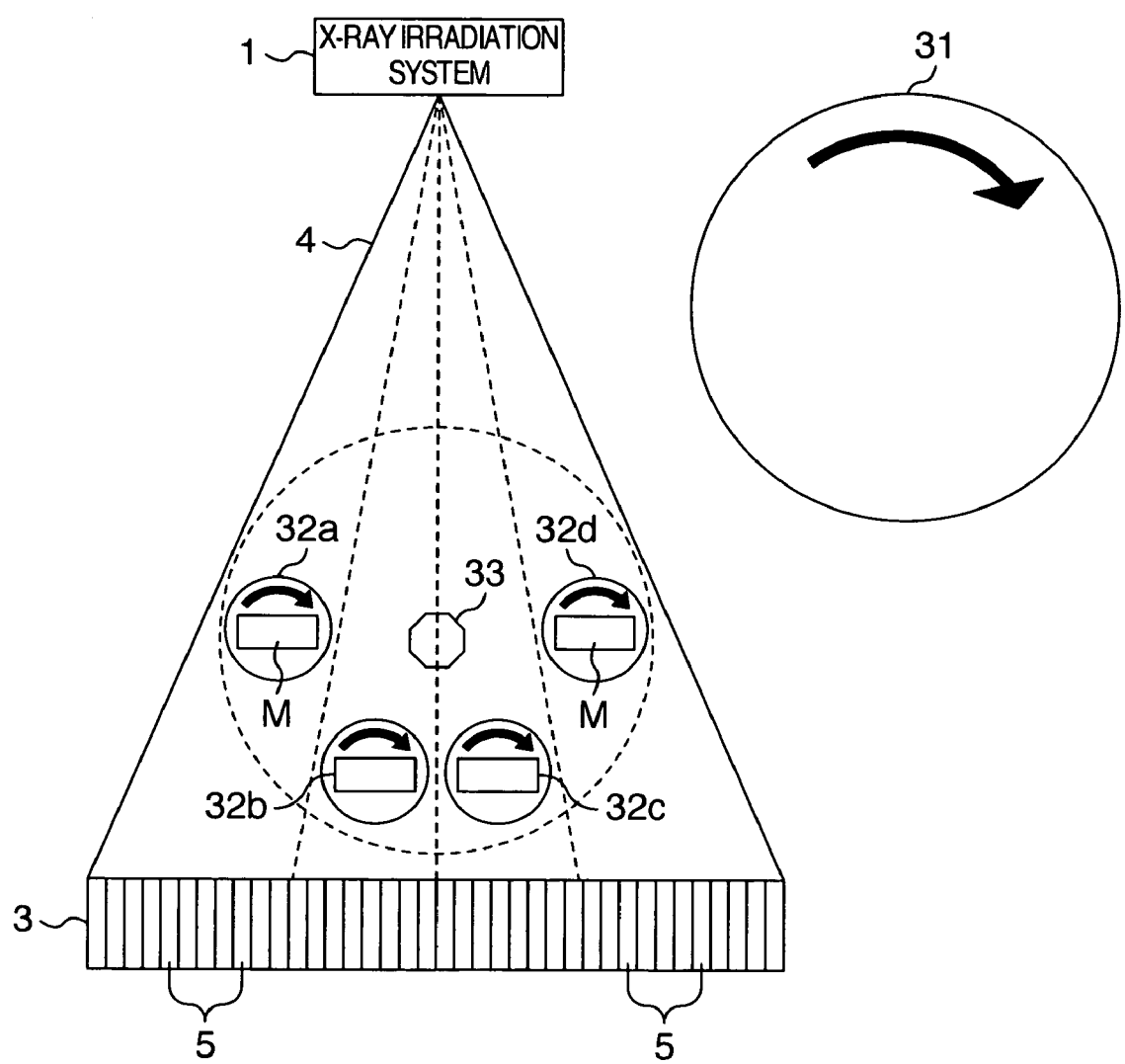
FIG. 3 is a diagram schematically showing the configuration of a computed tomography system in accordance with a third embodiment.

FIG. 3 schematically shows the configuration of an X-ray computed tomography system that is a computed tomography system in accordance with a third embodiment. The X-ray computed tomography system in accordance with the present embodiment comprises one large turn table 31 and a plurality of, specifically, four small turn tables 32*a* to 32*d*. The large turn table 31 and the small turn tables 32 can be selectively used. Specifically, the small turn tables 32*a* to 32*d* are fixedly arranged so as to be covered by the region of irradiation with the fan beams 4 as in the case of the first embodiment. On the other hand, the large turn table 31 can be installed above the small turn tables 32*a* to 32*d* as required via an attachment portion 33 provided in a central portion in the region of irradiation with the fan beams 4.

Thus, according to the present embodiment, the large turn table 31 and the small turn tables 32 are selectively used to enable image pickup in accordance with the size of the testing object as in the case of the second embodiment. For small testing objects, the present embodiment can increase the image pickup efficiency for a plurality of image pickup targets.

The present invention enables images of a plurality of testing objects to be simultaneously picked up without increasing the volume of noise or the scale of the system, thus enabling high-quality tomographic images to be efficiently picked up. The present invention can be widely utilized in the field of X-ray computed tomography systems.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A computed tomography system comprising:
   a radiation irradiation system that provides a radiation that is a beam having a region of irradiation spreading radially in a direction of irradiation;
   a turn table system on which a testing object is placed, said turn table system comprising one large turn table and a plurality of small turn tables, wherein the large and small turn tables are selectively used; and
   a radiation detection system that detects the radiation having penetrated the testing object, the radiation being applied to the testing object being rotated using the turn table system, the radiation detection system detecting the radiation in the irradiation to acquire radiation penetration data for image reconstruction.

2. The computed tomography system according to claim 1, wherein the plurality of small turn tables are installed on the large turn table, as required, via attachment portions provided on the large turn table.

3. The computed tomography system according to claim 1, wherein the plurality of small turn tables are arranged in the region of irradiation with the radiation beam, and the large turn table is installed above the plurality of small turn tables, as required, via an attachment portion provided in the region of irradiation with the radiation beam.

* * * * *